(12) United States Patent
Eriksson et al.

(10) Patent No.: US 8,623,031 B2
(45) Date of Patent: Jan. 7, 2014

(54) SYSTEM AND METHOD FOR TRANSPLANTATION OF DERMAL TISSUE

(75) Inventors: Elof Eriksson, Wellesley, MA (US);
Royce Johnson, Universal City, TX (US); Ajit Mishra, Elkton, MD (US);
Michael Girouard, San Antonio, TX (US); Makoto Ohira, Westborough, MA (US); Jonathan Kagan, Hopkins, MN (US)

(73) Assignee: KCI Licensing, Inc., San Antonio, TX (US)

( * ) Notice: Subject to any disclaimer, the term of this patent is extended or adjusted under 35 U.S.C. 154(b) by 199 days.

(21) Appl. No.: 12/705,668

(22) Filed: Feb. 15, 2010

(65) Prior Publication Data

US 2010/0145360 A1   Jun. 10, 2010

Related U.S. Application Data

(62) Division of application No. 10/673,661, filed on Sep. 29, 2003, now Pat. No. 7,666,134.

(60) Provisional application No. 60/414,133, filed on Sep. 28, 2002.

(51) Int. Cl.
*A61B 17/50* (2006.01)

(52) U.S. Cl.
USPC ........................................................ 606/132

(58) Field of Classification Search
USPC ........... D7/678, 679; 241/93, 273.3; 606/131, 606/167, 180
See application file for complete search history.

(56) References Cited

U.S. PATENT DOCUMENTS

| | | | | |
|---|---|---|---|---|
| 3,037,509 | A | 6/1962 | Schutz | 606/132 |
| 3,640,279 | A | 2/1972 | Brown et al. | 606/132 |
| 3,824,745 | A * | 7/1974 | Hutchins | 451/359 |
| 4,285,618 | A * | 8/1981 | Shanley, Jr. | 407/54 |
| 5,030,201 | A | 7/1991 | Palestrant | 604/22 |
| 5,152,757 | A | 10/1992 | Eriksson | 604/305 |
| 6,039,760 | A | 3/2000 | Eisenberg | 623/15.12 |
| 6,050,972 | A * | 4/2000 | Zadno-Azizi et al. | 604/97.01 |
| 6,391,034 | B1 * | 5/2002 | Adamson et al. | 606/131 |
| 6,673,081 | B1 * | 1/2004 | Tavger et al. | 606/131 |
| 7,134,437 | B2 | 11/2006 | Bonutti | 128/898 |
| 7,427,284 | B2 | 9/2008 | Seedhorn et al. | 606/79 |

FOREIGN PATENT DOCUMENTS

| | | |
|---|---|---|
| JP | S63-56244 | 3/1988 |
| JP | H01-235538 | 9/1989 |
| JP | H07-75485 | 3/1995 |
| WO | WO 98/09574 | 3/1998 |
| WO | WO 01/39694 | 6/2001 |

OTHER PUBLICATIONS

Office Communication, issued in Japanese Patent Application No. 2006-528311, dated May 11, 2010.

(Continued)

*Primary Examiner* — Ryan Severson
*Assistant Examiner* — Ashley Fishback

(57) ABSTRACT

A dermal tissue transplantation system combining a tissue particle harvester, a tissue particle collector, and a chambered dressing. The system provides a harvester capable of harvesting tissue from a donor site on the order of about 100 microns. The integrated tissue particle collector provides a means for collecting the harvested tissue for in situ cultivation in a chambered dressing at the wound site.

16 Claims, 11 Drawing Sheets

(56) References Cited

OTHER PUBLICATIONS

Office Communication, issued in European Application No. 04789154.4, dated Jul. 14, 2008.
Office Communication, issued in U.S. Appl. No. 10/673,661, dated Apr. 29, 2009.
Office Communication, issued in U.S. Appl. No. 10/673,661, dated Oct. 28, 2008.
Office Communication, issued in U.S. Appl. No. 10/673,661, dated May 28, 2008.
Office Communication, issued in U.S. Appl. No. 10/673,661, dated Nov. 8, 2007.
Office Communication, issued in U.S. Appl. No. 10/673,661, dated May 30, 2007.
Office Communication, issued in U.S. Appl. No. 10/673,661, dated Jan. 4, 2007.

* cited by examiner

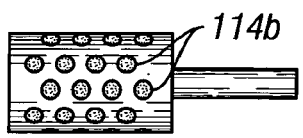
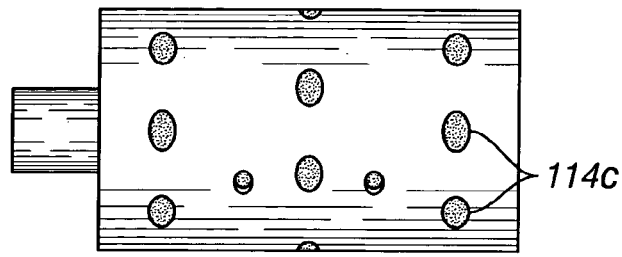
FIG. 6  FIG. 7A
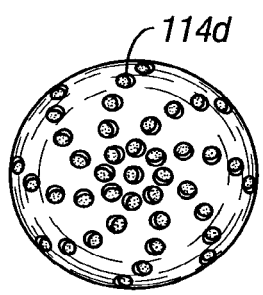
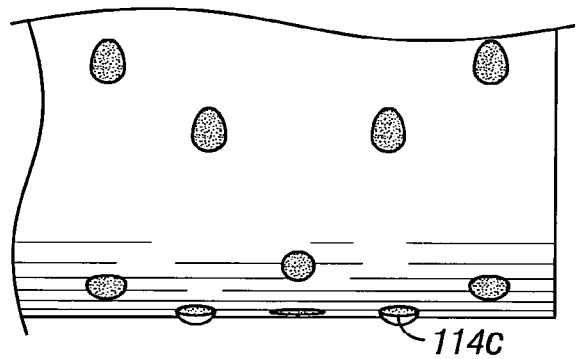
FIG. 8  FIG. 7B
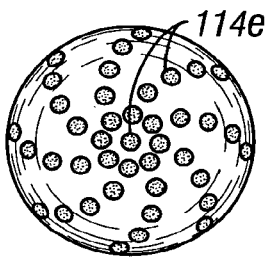
FIG. 9

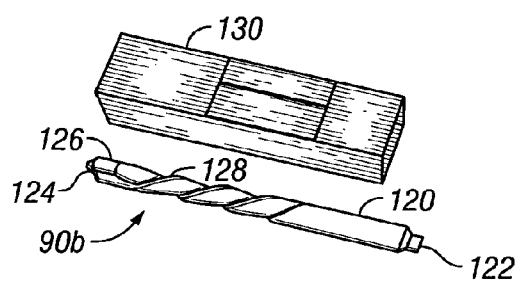 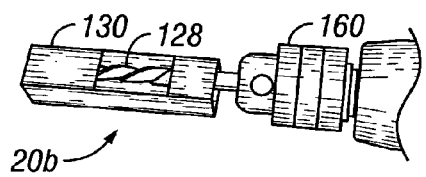
FIG. 10A  FIG. 10B
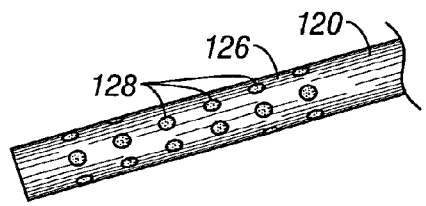 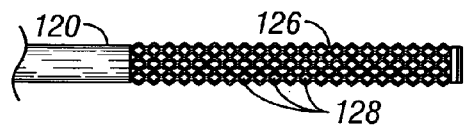
FIG. 11  FIG. 12
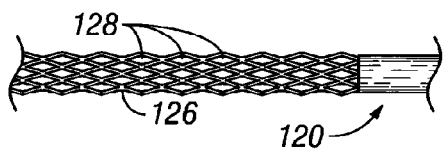 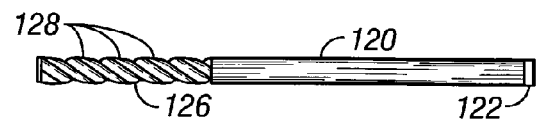
FIG. 13  FIG. 14

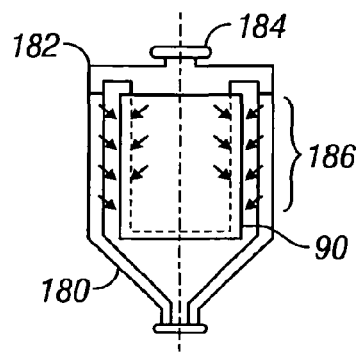
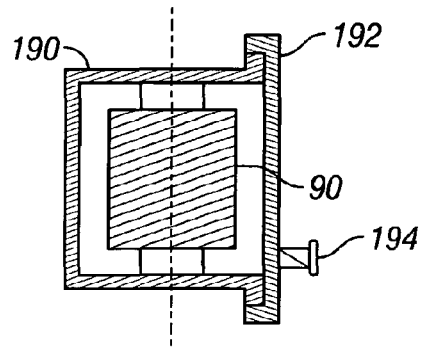
FIG. 21A  FIG. 21B
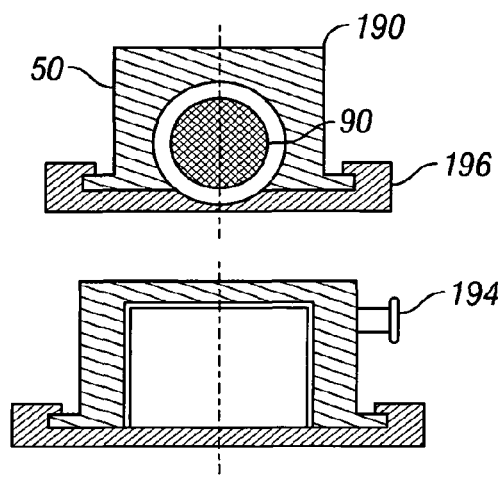
FIG. 21C
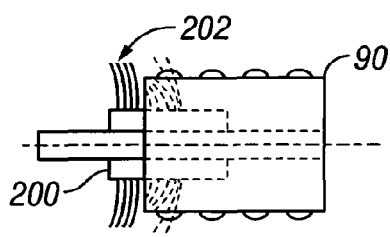
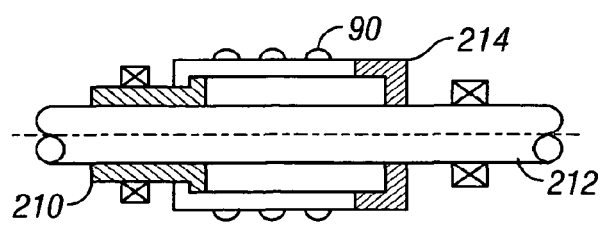
FIG. 22  FIG. 23

SYSTEM AND METHOD FOR TRANSPLANTATION OF DERMAL TISSUE

CROSS-REFERENCE TO RELATED APPLICATION AND PRIORITY CLAIM

The present application is a divisional of co-pending U.S. patent application Ser. No. 10/673,661, filed Sep. 29, 2003, which claims priority to U.S. Provisional Application No. 60/414,133, filed Sep. 28, 2002. The entire text of each of the above-referenced disclosures is specifically incorporated by reference herein without disclaimer.

FIELD OF THE INVENTION

The invention relates to a dermal tissue transplantation system. More particularly, this invention relates to a system for obtaining, processing, collecting, and applying tissue samples for purposes of transplantation

BACKGROUND OF THE INVENTION

Traditional skin grafting is accomplished by taking a thin slice of dermal tissue from a donor site in order to cover a wound site, such as a burn area. In some instances, the slice of dermal tissue is meshed to expand its size, creating a meshed graft. Traditional devices used to harvest the tissue from the donor site include dermatomes, which function in many respects similar to a cheese slicer.

Traditional meshed grafting techniques have been shown to yield 90% viability at the donor site. A slightly lower viability rate occurs for non-meshed sheet grafts, mostly due to fluid accumulation under the sheet graft. Factors that lead to graft failure include poor circulation, unclean wounds, patient interference with the graft dressing, obesity, and smoking. Additionally, in at least approximately 10% of cases, infection at the donor site occurs. Although such donor site infections are not likely related to graft failure at the wound site, they still pose problems for both the patient and caregiver.

Traditional meshing techniques yield a most favorable expansion ratio of 6:1. (for example a 1 $cm^2$ donor site can cover a 6 $cm^2$ wound site). While greater ratios of 9:1 and 12:1 are certainly possible, there is also a significant delay in epithelialization with such ratios.

Micro grafting techniques, in which the donor tissue is actually minced in order to achieve a greater than 10:1 expansion ratio, are known in the art. Such techniques allow for a much greater coverage area from a small donor site. However, traditional techniques are cumbersome, and often the viability of the cells is compromised to such an extent that sometimes less than 50% of the cells are viable when applied to the wound site.

It is therefore an object of this invention to provide a simpler grafting procedure, improve micro-graft viability ("take"), reduce the bio-burden at the wound site by better preparation of the wound bed prior to grafting, improve the cosmetics of grafts as compared to meshed grafts, and reduce the size of the donor site.

Additional objects of the present invention include a significant reduction in the size of the donor site as compared to traditional mesh-graft procedures; minimizing scarring of the graft site as compared to traditional mesh-graft procedures; improvement of the pliability of tissue in the graft site; improvement of the cosmetic appearance of the graft site as compared to current methods; and improvement of graft "take."

It is still a further object of this invention to provide a grafting technique that does not extend the healing time as compared with traditional mesh-grafts, while also reducing the cost and time required to complete the procedure.

SUMMARY OF THE INVENTION

In accordance with the foregoing objects, the present invention generally comprises a skin harvester for obtaining tissue from a donor site, a tissue particle collector for collecting tissue from the harvester, and a chambered dressing for propagating the collected tissue in situ at a wound site.

The foregoing has outlined some of the more pertinent objects of the present invention. These objects should be construed to be merely illustrative of some of the more prominent features and applications of the invention. Many other beneficial results can be attained by applying the disclosed invention in a different manner or by modifying the invention as will be described. Accordingly, other objects and a fuller understanding of the invention may be had by referring to the following Detailed Description of the Invention, which includes the preferred embodiment

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which:

FIG. 6 is an illustration of a "TI" type cutting features on a rotary drum-type cutting tool of the present invention.

FIGS. 7A and 7B illustrate "scallop" type cutting features with hypo-tubes on a rotary drum type cutting tool of the present invention.

FIG. 8 illustrates "square scallop" type cutting features useful for the cutting surface of a rotary drum-type cutting tool of the present invention.

FIG. 9 illustrates "round scallop" type cutting features useful for the cutting surface of a rotary drum-type cutting tool of the present invention.

FIGS. 10A and 10B illustrate a rotating shaft-type tissue cutter tool and harvester housing (A), and the rotating shaft-type tool installed in a type of tissue harvester assembly (B). The tool is a side cutting bit installed in a shear block type harvester housing of the present invention.

FIG. 11 illustrates a fine scallop hypo-tube rotating shaft-type tissue cutter tool of the present invention.

FIG. 12 illustrates a course scallop hypo-tube rotating shaft-type tissue cutter tool of the present invention.

FIG. 13 illustrates a course scallop solid shaft-type tissue cutter tool of the present invention.

FIG. 14 illustrates an alternative side cutting bit shaft-type tissue cutter tool of the present invention.

FIGS. 21A, 21B, and 21C are cross-sectional views of a separate flushing container tissue particle collector of the present invention.

FIG. 22 is a cross-sectional view of a bristled plunger tissue particle collector of the present invention.

FIG. 23 is a cross-sectional view of a standard plunger tissue particle collector of the present invention.

DESCRIPTION OF THE INVENTION

Figure 1:
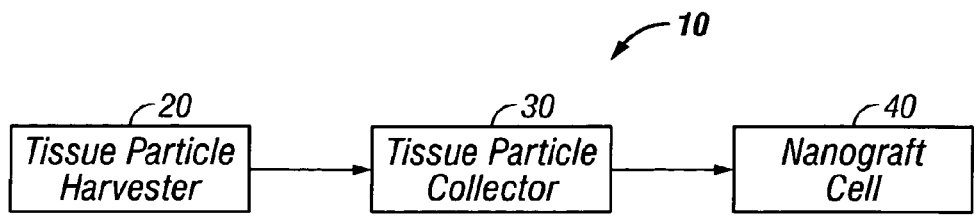
FIG. 1 is a block diagram generally illustrating the dermal tissue nano-grafting system of the present invention.

Although those of ordinary skill in the art will readily recognize many alternative embodiments, especially in light of the illustrations provided herein, this detailed description is exemplary of the preferred embodiment of the present invention as well as alternate embodiments, the scope of which is limited only by the claims that may be drawn hereto.

Referring now to the drawings, the details of preferred embodiments of the present invention are graphically and schematically illustrated. Like elements in the drawings are represented by like numbers, and any similar elements are represented by like numbers with a different lower case letter suffix.

As illustrated in FIG. 1, the dermal tissue nano-grafting system 10 of the present invention comprises three main components: a tissue particle harvester assembly 20 for cutting tissue particles from dermal tissue; at issue particle collector 30 for receiving, separating and collecting the tissue particles; and a chambered dressing 40 for receiving the collected tissue particles and culturing the growth of a dermal tissue graft. The ideal size of the tissue collected is about 50-300 microns; with the median particle size about 100 microns. The tissue particle harvester assembly 20 excises tissue particles of an appropriate size range from a dermal tissue source. The tissue particle collector 30 receives the harvested tissue particle, collects and holds them in a proper environment to maintain their viability prior to seeding the particles in a chambered dressing 40. The chambered dressing 40 of the present invention is a type of tissue culture device for growing dermal graft tissue in situ on a skin graft site. Exemplary devices that may be used for the chambered dressing 40 are described in U.S. Pat. No. 5,152,757, issued on Oct. 6, 1992 to Eriksson, entitled "System For Diagnosis And Treatment Of Wounds" and U.S. Provisional patent application Ser. No. 10/361,341, entitled "Environmental Control Device For Tissue Treatment" filed on Feb. 11, 2002, by Johnson, et al., the disclosures of which are incorporated by reference herein as though fully set forth.

Figure 2:
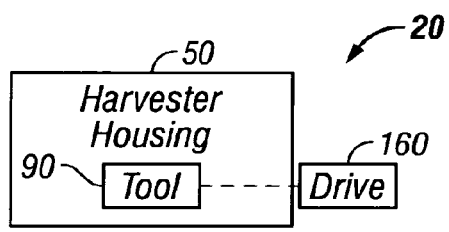
FIG. 2 is a block diagram generally illustrating the tissue harvester assembly of the present invention.
Figure 3:
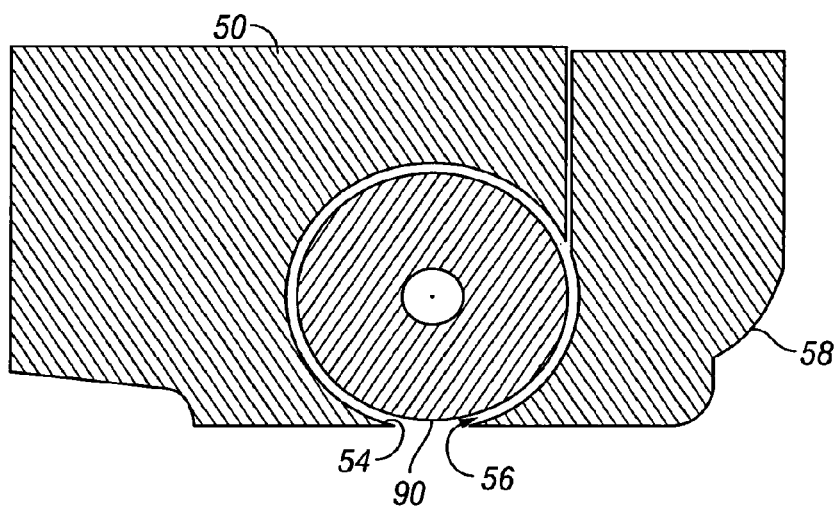
FIG. 3 is a cross-sectional side view of a harvester housing showing an interior space into which a tissue-cutting tool is received.
Figure 4A:
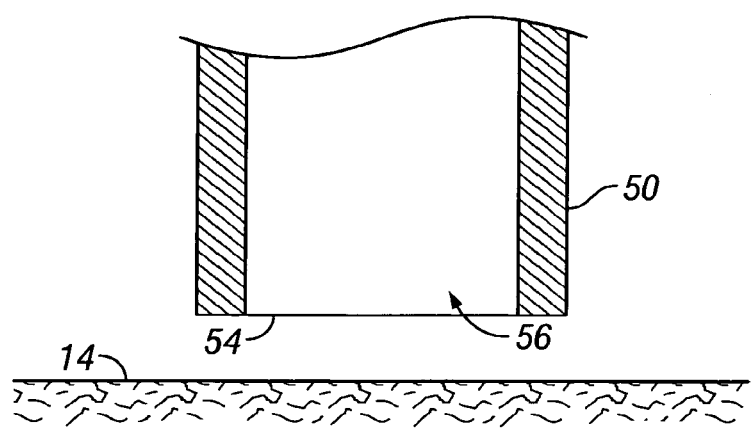
FIGS. 4A and 4B are cross-sectional front views of a harvester housing illustrating the interface of the housing with the tissue source to be harvested.
Figure 4B:
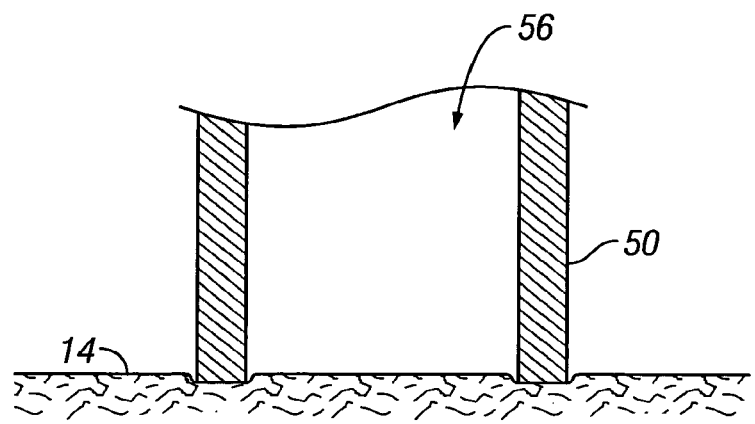

As illustrated in FIG. 2, the tissue particle harvester assembly 20 comprises a harvester housing 50, a tissue cutting tool 90 and a drive means 160. As exemplified in FIG. 3, the harvester housing 50 has a tissue opening 54 accessing an interior space 56, into which a tissue-cutting tool 90 is received. As further exemplified in FIGS. 4A and 4B, the harvester housing 50 interfaces with the dermal tissue source 14 from which tissue particles are to be harvested, and holds the tissue cutting tool 90 in a proper position relative to, the dermal tissue 14. The tissue opening 54 of harvester housing 50 serves as an orifice for pressing against and receiving a dermal tissue layer of the tissue source 14.

A proper position of the cutting tool 90 relative to the dermal tissue source 14 relates to the depth of penetration of the cutting tool 90 into the layers of the dermal tissue 14. A proper positioning of the cutting tool 90 facilitates excising tissue particles of an appropriate size. The depth of penetration of the cutting tool 90 into the surface of the tissue 14 should range from about 0.01 mm to about 0.9 mm, and preferably should be about 0.1 mm+/−0.05 mm, depending on the type of cutting tool 90 being used. The depth of penetration can be modified by a number of means known to one of ordinary skill in the art, including adjusting the proximity of the cutting tool to the tissue opening 54 in the housing 50, and by adjusting the cutting aspect 118 (see FIG. 5B) of the cutting features 114 of the cutting tool 90. The cutting aspect 118 of a cutting feature 114 is the reach of a cutting feature 114 beyond the cutting surface 94 of the tool 90. The harvester housing 50 can include a depth adjustment means for adjusting the proximity of the cutting tool to the tissue opening 54 in the housing 50. Again, such adjustment means are known to and practicable in the present harvester assembly 20 by the ordinary skilled artisan. For example, as in FIG. 3, such adjustment means 58 can be made by moving an edge of the tissue opening 54 closer to, or farther away, from the cutting tool 90.

Figure 5A:
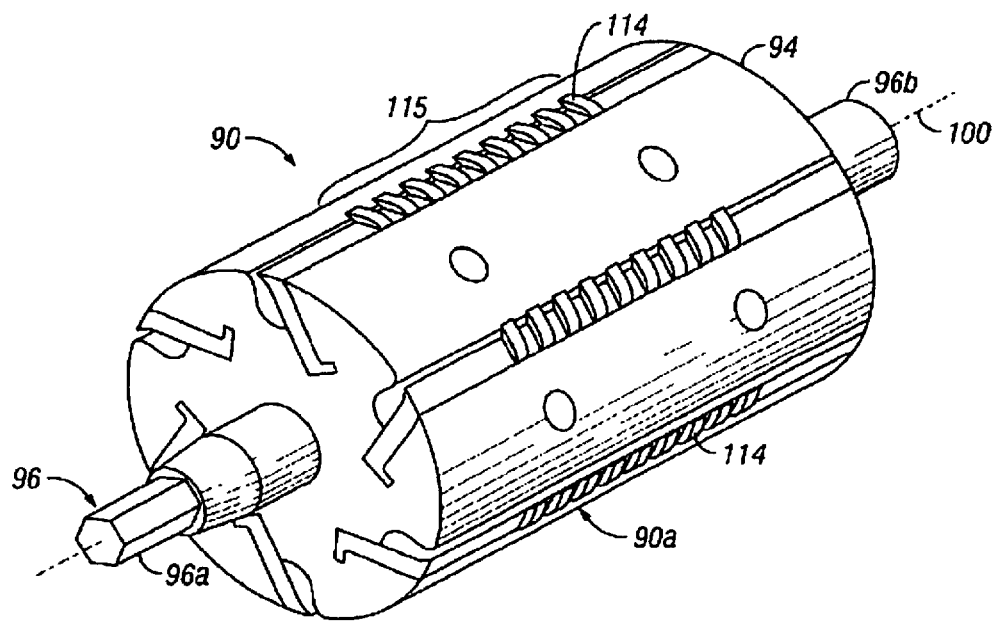
FIGS. 5A and 5B are a perspective view (A) and an end view (B) of a rotating shaft-type tissue cutter.
Figure 5B:
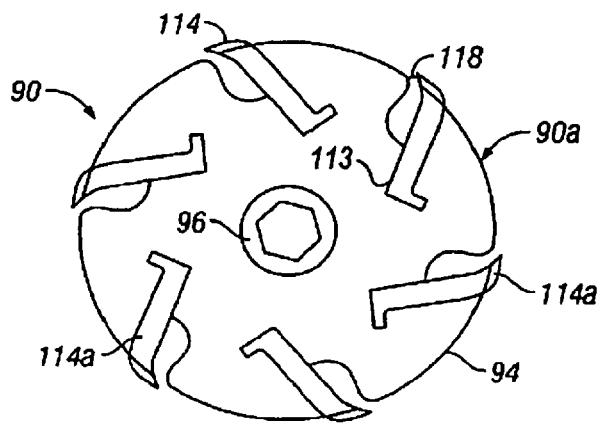

As exemplified in FIGS. 5A and 5B, a tissue cutting tool 90 has a cutting surface 94 and cutting features 114 which project from the cutting surface 94 and impinges on the tissue source 14 to cut or excise tissue particles of an appropriate size from the tissue 14 when the cutting tool 90 is rotated. A rotatable shaft 96 extends from the tool 90 along its axis of rotation 100. The rotatable shaft 96 has a drive end 96a for engaging a drive means and a tool end 96b for mounting the cutting surface 94. The cutting tool shaft drive end 96a is receivable by a drive means 160 (e.g., see FIGS. 10B and 16A & 16B) to impart rotation to the cutting tool 90. The rotating drum type cutting tool 90a shown in FIGS. 5A and 5B has a tool end shaft 96b that extending from the tool 90 along the axis of rotation 100 opposite the drive end 96a. In FIGS. 5A and 5B, the drum of the tool 90 has it axis disposed coaxially with the axis 100 of the rotatable shaft 96.

The cutting surface 94 of a rotating drum type cutting tool 90a can be practiced with any of a variety of different cutting features 114 selectable by the ordinary skilled artisan. In FIGS. 5A and 5B, the cutting features are a plurality of sharpened fingers 114a inserted into L-shaped slots 113, projecting from the cutting surface 94 spaced apart and in rows, forming a serrated blade 115. Examples of other types of cutting features 114 practicable on the drum-type cutting tool 90a include: "TI" type cutting features 114b on a rotary drum type cutting tool (see FIG. 6); "scallop" type cutting features 114c with hypo-tubes on a rotary drum type cutting tool (see FIGS. 7A and 7B); and "square scallop" type cutting features 114d (see FIG. 8) and "round scallop" type cutting features 114 e (see FIG. 9), both useful for the cutting surface of a rotary drum type cutting tool 90 a.

Not all tissue-cutting tools 90 practicable in the present harvester assembly 20 are rotary drum type cutting tools 90a. For example, rotating shaft cutting tools 90b (see FIGS. 10-14) may be used. As exemplified in FIG. 10A, a rotating shaft cutting tool 90b comprises a rotatable shaft 120 having a drive end 122 for engaging the drive means 50 and a tool end 124 for mounting the tissue cutting surface 126 and cutting features 128. FIGS. 10A and 10B illustrate a rotating shaft-type tissue cutter tool 90b and harvester housing 130, and the rotating shaft-type tool 90b installed in a type of tissue harvester assembly 20b and connected to a drive means 160. The tool 90b has a side cutting bit feature 128a and is installable in a shear block type harvester housing 130. Other configurations of rotating shaft-type tissue cutter tools 90b are practicable in the present harvester assembly 20b. Examples include: a fine scallop hypo-tube rotating shaft-type tissue cutter tool (FIG. 11); a course scallop hypo-tube rotating shaft-type tissue cutter tool (FIG. 12); a course scallop solid shaft-type tissue cutter tool (FIG. 13); and alternative side cutting bit shaft-type tissue cutter tools (FIG. 14).

Figure 15:
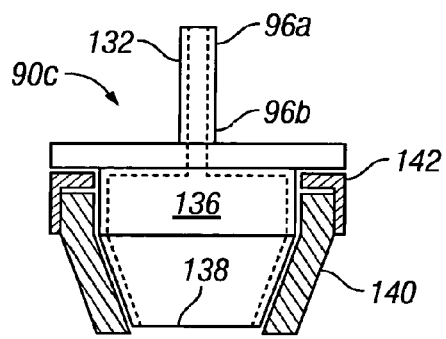
FIG. 15 is a partial cross-sectional end view of the housing and tissue-cutter tool of an end-mill type tissue harvester assembly of the present invention of the present invention.

Other types of cutting tools 90 such as an end mill type cutting tool 90c (see FIG. 15) are also practicable in the present invention. The rotating drum and shaft tissue cutting tools 90a & 90b noted above can have both a drive end 96a and a tool end 96b. However, an end mill type cutting tool 90c will have only a shaft drive end 96a. A rotating end-mill cutting tool 90c comprises a rotatable shaft 132 having a drive end 96a for engaging the drive means 160 and a tool end 96b for mounting a cutting drum 136. The cutting drum 136 is cylindrical and has an axis disposed coaxially with the drive and tool shaft ends 96a and 96b. The tool end 96b is attached at one end of the cutting drum 136 and the other end of the cutting drum 136 mounts a tissue cutting surface 138. The tissue-cutting surface can be constructed to have cutting features 114 similar to those practicable on the rotating drum type cutter 90a noted above. One of ordinary skill in the art is readily able to select from and adapt said cutting features 114 for incorporation onto the cutting surface 138 of a rotating end-mill cutting tool 90c of the present invention 10. The drum 136 has an outer circumferential surface that is closely receivable in a width of the interior space of the end mill housing 140 associated depth alignment means 142. The cutting drum 136 of the end mill tissue cutting tool 90c illustrated in FIG. 15 is a tapered cylinder proximate its tissue cutting surface 138. The benefit of this taper is that centrifugal force can facilitate the migration of excised tissue particles passing through the cutting surface 138 into the interior of the drum (shown in phantom) and up the interior walls and away from the cutting surface 138. This will help to prevent clogging certain of the cutting features 114 with excised tissue particles.

Figure 16:
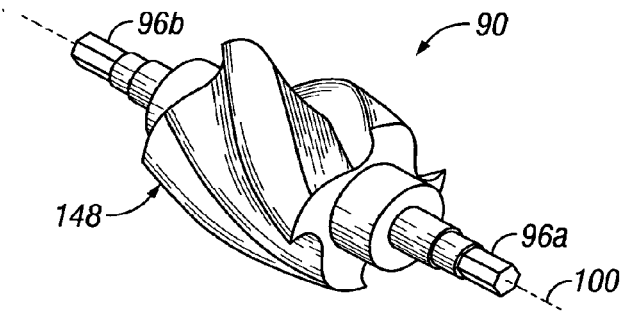
FIG. 16 is a perspective view of a modified rough cutting end-mill cutter tool of the present invention.
Figure 17:
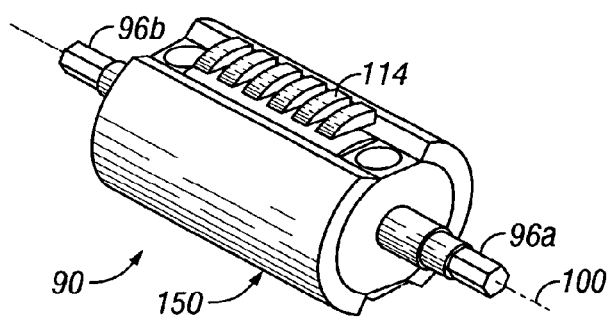
FIG. 17 is a perspective view of a razor cutter with serrations cutter tool of the present invention.

Alternative cutting tools 90, as shown in FIGS. 16 and 17, may be utilized include a modified rough-cutting end mill 148 and a razor cutter with serrations 150. Such a modified end mill 148 exhibits cutting characteristics of a typical end mill cutting tool as shown in FIG. 15, however the modified end mill 148 exhibits a cylindrical shape and an axis 100 disposed coaxially with the drive and tool shaft ends 96a & 96b, similar to the rotating shaft cutter of FIG. 5A.

Figure 18A:
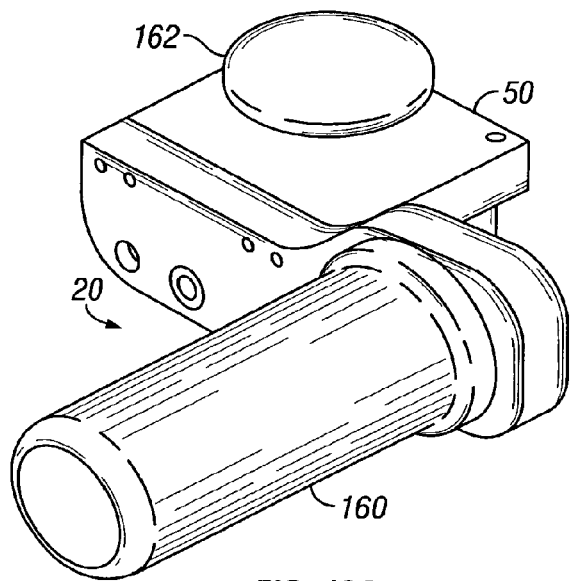
FIGS. 18A and 18B are a top perspective (A) and a bottom perspective (B) view of a rotating drum cutter type tissue harvester assembly, with integral drive means of the present invention.
Figure 18B:
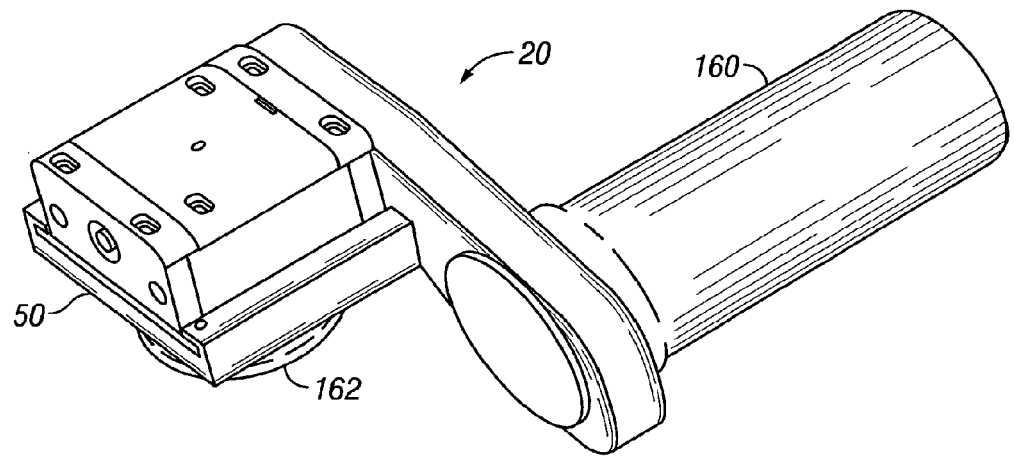

The drive means 160 is typically a drive motor of some type (e.g., electric or pneumatic) for rotating the tissue-cutting tool in the harvester housing 50 & 140. The drive means 160 may be integral to (see FIGS. 18A and 18B) or separate from (see FIG. 10B) the harvester housing 50 & 140. A handle 162 may be connected or formed to the housing 50 in order for a user to more easily grasp and position the harvester assembly 20.

Figure 19:
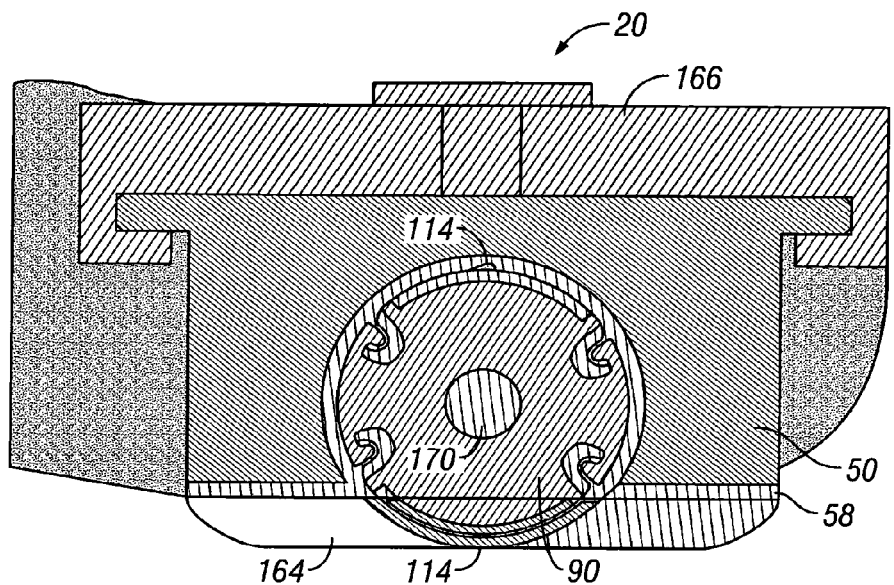
FIG. 19 is a cross-sectional view of the cutter housing area of the harvester assembly of the present invention.

As is illustrated in FIG. 19, a port 170 may be provided within the cutter 90 to draw tissue that has been collected by the cutter 90 out of the housing 50. While the port 170 has been shown in the center of the cutter 90 along its axis of rotation in this embodiment, it is to be understood that multiple mechanisms for removing tissue from the housing are envisioned and described further herein. A housing mounting 166 is provided for stability and support to the user during operation of the harvester 20. Skid plates 164 are provided to ease in positioning of the cutter 90 at the tissue site, and to further aid in adjustment of the cutter 90 depth, especially when a shim stack 58, or other adjustment means known in the art, are provided external of the cutter 90.

Figure 20A:
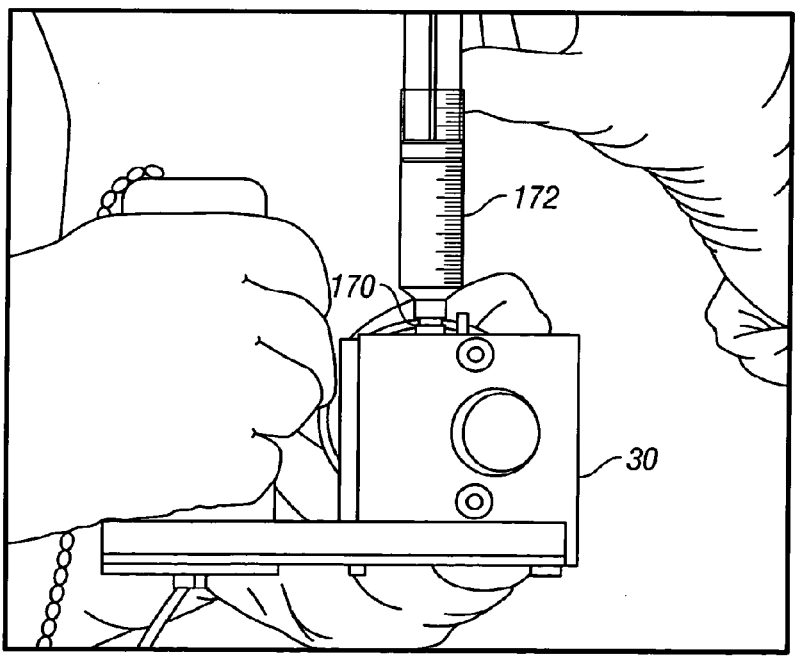
FIGS. 20A, 20B, and 20C are side angle views of the tissue particle harvester and collector in use.
Figure 20B:
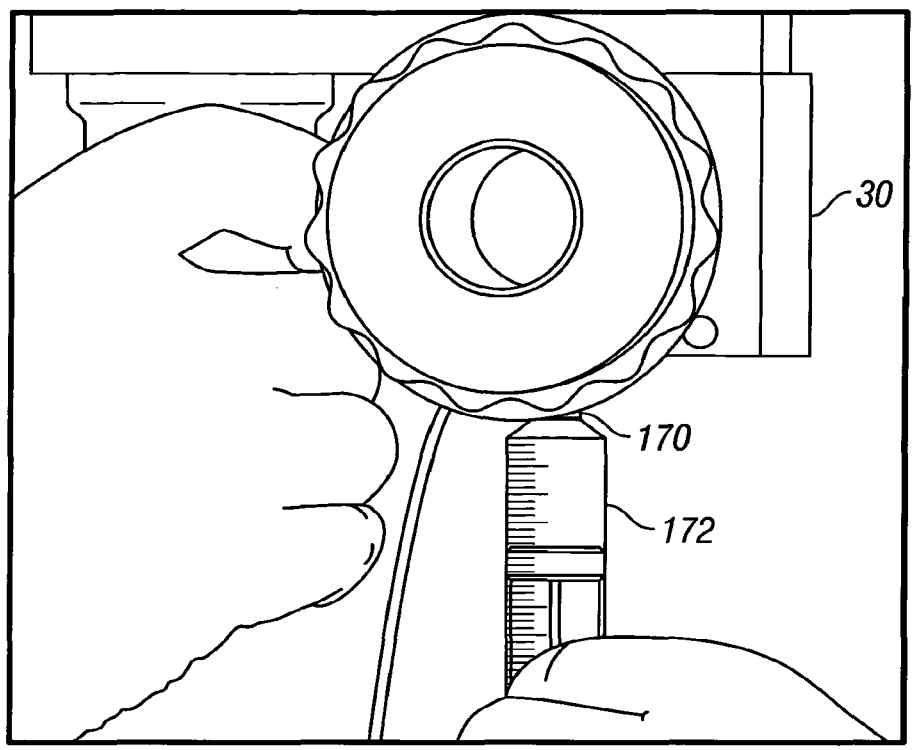
Figure 20C:
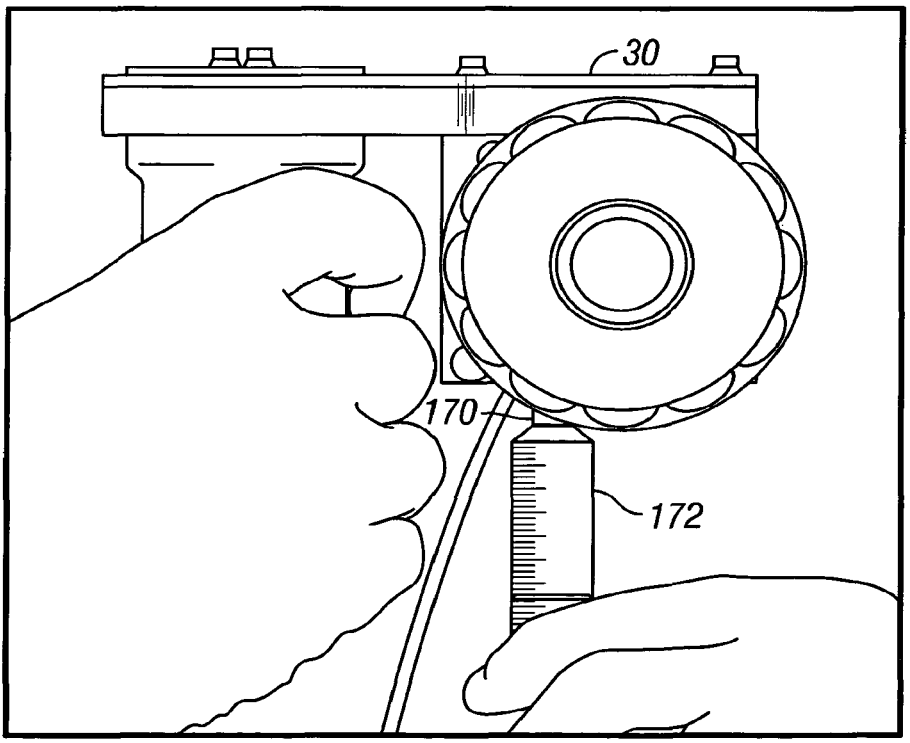

FIGS. 20A, 20B, and 20C illustrate a tissue particle collector 30, which may be comprised of a port 170 positioned within or near the drive means of the cutter 90, and which may be accessible my a particle retriever 172, such as a syringe. The particle retriever 172 may then be used to inject or otherwise instill the tissue collected into a nanograft cell 40, as shown in FIG. 1. Various mediums may be utilized to suspend the tissue within the tissue particle collector 30, and subsequently the nanograft cell 40. Such mediums may include, but are not necessarily limited to, saline.

Alternative embodiments of the tissue particle collector 30 for collecting tissue from the tissue particle harvester are illustrated in FIGS. 21-27. A separate flushing container 180, as illustrated in FIG. 21A, may be utilized to retrieve tissue from the cutter 90. The cutter 90 is removed from the harvester housing 50, and placed into the flushing container 180. A cap 182, or other cover, is screwed or otherwise secured to the container 180. A liquid medium, such as saline, is then flushed through a port 184 or luer, which may be integrated with the cap 182, or otherwise introduced into the container 180, and is directed towards the inner diameter and outer diameter of the cutter 90 by jets 184 or channels within the container 180.

An integral flushing container 190, as illustrated in FIG. 21B, allows for collection of tissue without removal of the cutter 90 from its housing 50. In this embodiment, the cutter 90 has a solid filled core. A gasketed cap 192 is fitted over the integral flushing container 190, which may be the housing 50 having a receptor for the gasket cap 192, after tissue is cut from the donor site. The housing 50, with the cutter 90 in place, is removed from the tissue particle harvester 20 and fluid, which may be saline, is injected into the flushing container 190 through a luer fitting 194, or port. The flushing container 190 is manually agitated, by hand or by a mechanical agitator known in the art. After agitation, the tissue that has been cut by the cutter 90 is now suspended in the fluid which has been injected, at which point it may be drawn out of the integral flushing container 190 through the luer fitting 194 by means of a syringe or similar device known in the art.

An alternative embodiment of an integral flushing container 190 is illustrated in FIG. 21C. A core filled cutter 90 is utilized to remove tissue from the donor site. A cap 196, which may be comprised of silicone or a material of similar physical characteristics is placed over the open-cutting face of the housing 50. The housing may include a luer for injecting fluid, such as saline, which is then agitated by running the motor of the cutter 90. The agitation results in suspension of the tissue cut by the cutter 90 in the fluid, which may then be drawn out by through the luer 194 by a syringe or similar device, for insertion into a chambered dressing 40.

Collection of tissue from the cutter 90 may also be accomplished by use of a bristled plunger 200, as shown in FIG. 22.

The bristled plunger 200 is insertable into the inner diameter of a cutter 90 having a hollow core. After collection of tissue by the cutter 90, the plunger 200 is moved, manually or mechanically, into the inner diameter of the cutter 90. Bristles 202 draw out the tissue that has been collected in the inner diameter of the cutter 90 as the plunger is retracted from the inner diameter of the cutter 90. The plunger 200 may be retractable into an adjacent container (not shown) that may be filled with a fluid, such as saline, for suspension of the tissue collected from the cutter 90. A luer (not shown) may be incorporated into the adjacent container for retrieval of the tissue suspended fluid by a syringe or similar device, and for injection of the fluid prior to tissue collection.

In a further alternative embodiment as illustrated in FIG. 23, a standard plunger 210 rides over the shaft 212 of the cutter 90 assembly. The shaft 212, plunger 210, and cutter 90 all rotate together during operation of the harvester assembly 20. After tissue has been removed from the donor site by the cutter 90, the plunger 210 is moved across the inner diameter of the cutter 90 towards a removable end cap 214. The end cap 214 is removed from the harvester assembly 20 so the tissue may be removed or flushed out by means of a syringe or other process well known to those skilled in the art.

Figure 24:
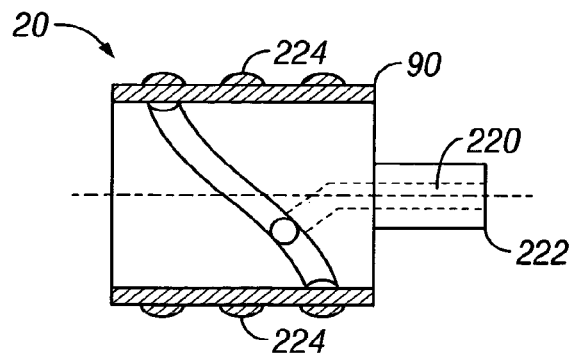
FIG. 24 is a cross-sectional view of an internal flushing channels embodiment of the tissue particle collector of the present invention.

Still a further embodiment of the tissue particle collector 30 is the internal flushing channels 220 as illustrated in FIG. 24. An internal core 222 is positioned within the cutter 90. The core 222, which remains stationary during rotation of the cutter 90, is toleranced tightly to the inner diameter of the cutter 90 while still allowing for free rotation of the cutter 90. Tissue enters channels 222 through openings 224 in the cutter during operation of the cutter 90. Fluid is flushed through the channels 222 during operation of the cutter into a collection chamber (not shown) for later removal to the wound site. It is to be understood that the fluid may also be flushed through the channels 222 when the cutter 90 is not being operated.

Figure 25:
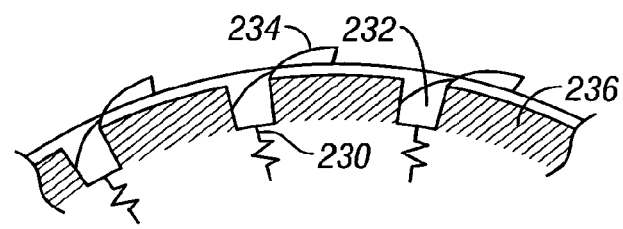
FIG. 25 is a cross-sectional view of a spring-loaded plunger tissue particle collector of the present invention.

FIG. 25 illustrates a spring-loaded plunger 230 that may be utilized to retrieve tissue particles from the cutter 90 after removal from the donor site. The spring-loaded plungers 230 are positioned within the recesses 232 of the cutting scoops 234 of a stationary core 236 of the cutter 90. After collection of tissue from the donor site, the core 236 is moved radially, or alternatively axially, until the plungers 230 pop out and remove tissue particles from the recesses 232. It is to be understood that the plungers 230 may be cam activated, or by similar mechanisms utilized by those skilled in the art, to extract tissue that has been collected within the recesses 232.

Figure 26:
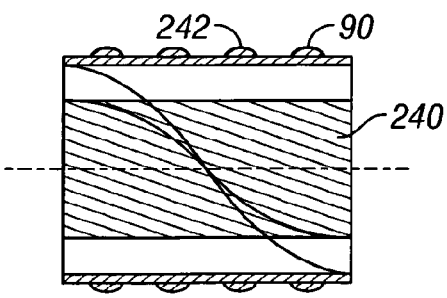
FIG. 26 is a cross-sectional view of a static internal screw tissue particle collector of the present invention.

Tissue may be removed from the harvester 20 by means of a static internal screw 240, as illustrated in FIG. 26. Such a screw 240, which may be described by those skilled in the art as a reverse Archimedes screw, is positioned within the inner diameter of the cutter 90. As the cutter 90 rotates and draws tissues into the cutter openings 242, the static internal screw 240 moves particles to one end of the cutter for collection by wiping the inner diameter of the cutter 90. It is envisioned that the screw 240 may be inserted after the tissue has been collected in order to wipe the inner diameter of the cutter 90, and move the tissue to one end of the cutter 90 for collection.

It is to be understood that manual agitation may also be utilized to remove tissue that has been collected by the cutter 90. The cutter 90 is removed from the harvester 20 and placed in a container holding fluid, such as saline or a similar fluid. The cutter 90 is spun within the container to remove particles into the fluid. The container may then be centrifuged to separate the tissue particles from the fluid or alternatively, the fluid may be passed through a filter to remove the tissue from the fluid.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

What is claimed is:

1. A tissue particle harvester assembly comprising:
   a housing including an internal flushing container;
   a port in the housing;
   a cap configured to fit over the internal flushing container;
   a rotatable shaft extending through a cylindrical body;
   a tissue cutting tool mounted on the rotatable shaft, wherein the tissue cutting tool is received within an open cutting face of the housing, and the cap is further configured to restrict fluid movement across the open cutting face of the housing;
   an electric motor coupled to the rotatable shaft; and
   a mechanical agitator.

2. The tissue particle harvester assembly of claim 1 wherein the port is configured to receive an injection of fluid.

3. The tissue particle harvester assembly of claim 2 wherein the fluid is saline.

4. The tissue particle harvester assembly of claim 2 wherein the fluid suspends a plurality of tissue particles within the flushing container during use.

5. The tissue particle assembly of claim 2 wherein the mechanical agitator is configured to agitate the fluid.

6. The tissue particle harvester assembly of claim 1 wherein the port is a luer fitting.

7. A tissue particle harvester assembly comprising:
   a housing;
   a tissue cutting tool received within the housing;
   a mechanical agitator; and
   an electric motor coupled to the tissue cutting tool, where:
      the tissue cutting tool comprises:
      a cylindrical body including a first end, a second end, and a cutting surface between the first and second end;
      a shaft extending through a center of the first end and the second end;
      a slot formed in the first end and extending into the cutting surface;
      a cutting feature inserted into the slot; and
      an internal core having at least one channel for fluid flow and configured to remain stationary with respect to the housing when the cutting surface is rotated with respect to the housing.

8. The tissue particle harvester assembly of claim 7 wherein the slot comprises an "L"-shaped portion when viewed from the first end.

9. The tissue particle harvester assembly of claim 7 wherein the cutting feature is a plurality of sharpened fingers.

10. The tissue particle harvester assembly of claim 7 wherein the tissue cutting tool comprises internal channels configured to flush tissue particles away from the cutting surface during use.

11. The tissue particle harvester assembly of claim 7 wherein the cutting feature comprises a serrated blade.

12. The tissue particle harvester assembly of claim 7 wherein the cutting feature extends from the slot to provide a cutting aspect.

13. The tissue particle harvester assembly of claim 12 further comprising an adjustment means coupled to the housing.

14. The tissue particle harvester assembly of claim 13 wherein the adjustment means is configured is configured to move towards or away from the cutting tool.

15. The tissue particle harvester assembly of claim 13 wherein the adjustment means is configured to adjust the cutting aspect.

16. The tissue particle harvester assembly of claim 7 wherein the electric motor is coupled to the shaft proximal to the first end.

* * * * *